United States Patent
Ting et al.

(10) Patent No.: US 7,854,754 B2
(45) Date of Patent: Dec. 21, 2010

(54) COOLING DEVICE FOR REMOVING HEAT FROM SUBCUTANEOUS LIPID-RICH CELLS

(75) Inventors: Joseph Ting, Acton, MA (US); Samuel W. Tolkoff, Brookline, MA (US); Timothy Robinson, Sandown, NH (US); Richard Wisdom, Mattapan, MA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 1182 days.

(21) Appl. No.: 11/359,092

(22) Filed: Feb. 22, 2006

(65) Prior Publication Data

US 2007/0198071 A1   Aug. 23, 2007

(51) Int. Cl.
  *A61F 7/00*    (2006.01)
(52) U.S. Cl. .......................... 607/96; 607/104; 607/112
(58) Field of Classification Search .................. 607/104, 607/112
  See application file for complete search history.

(56) References Cited

U.S. PATENT DOCUMENTS

| | | | |
|---|---|---|---|
| 3,093,135 A | 6/1963 | Hirschhorn | |
| 3,132,688 A | 5/1964 | Nowak | |
| 3,282,267 A | 11/1966 | Wiliam | |
| 3,502,080 A | 3/1970 | Hirschhorn | |
| 3,703,897 A | 11/1972 | Mack et al. | |
| 3,786,814 A | 1/1974 | Armao | |
| 3,827,436 A | 8/1974 | Stumpf et al. | |
| 3,942,519 A | 3/1976 | Shock | |
| 3,948,269 A | 4/1976 | Zimmer | |
| 3,986,385 A | 10/1976 | Johnston et al. | |
| 4,140,130 A | 2/1979 | Storm, III | |
| 4,202,336 A | 5/1980 | van Gerven et al. | |
| 4,266,043 A | 5/1981 | Fujii et al. | |
| 4,381,009 A | 4/1983 | Del Bon et al. | |
| 4,483,341 A | 11/1984 | Witteles | |
| 4,528,979 A | 7/1985 | Marchenko et al. | |

(Continued)

FOREIGN PATENT DOCUMENTS

CN   1817990 A   8/2006

(Continued)

OTHER PUBLICATIONS

Coban, "Ischemia-Reperfusion Injury of Adipofascial Tissue: An Experimental Study Evaluating early Histologic and Biochemical Alterations in Rats," Mediators of Inflammation, 2005, 5, 304-308.

(Continued)

*Primary Examiner*—Roy D Gibson
*Assistant Examiner*—Kaitlyn E Helling
(74) *Attorney, Agent, or Firm*—Perkins Coie LLP

(57) ABSTRACT

A cooling device for removing heat from subcutaneous lipid-rich cells of a subject having skin is provided. The cooling device includes a support having a first portion and a second portion. A first cooling element having a first heat exchanging surface is located at the first portion of the support. A second cooling element having a second heat exchanging surface is located at the second portion of the support. At least one of the first and second cooling elements is movable along the support and is configured to rotate for adjusting an angle between the first and second heat exchanging surfaces.

23 Claims, 9 Drawing Sheets

U.S. PATENT DOCUMENTS

| | | |
|---|---|---|
| 4,531,524 A | 7/1985 | Mioduski |
| 4,548,212 A * | 10/1985 | Leung .................. 600/549 |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,802,475 A | 2/1989 | Weshahy et al. |
| 4,832,022 A | 5/1989 | Tjulkov et al. |
| 4,846,176 A | 7/1989 | Golden |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,336,616 A | 8/1994 | Livesey et al. |
| 5,339,541 A | 8/1994 | Owens |
| 5,351,677 A | 10/1994 | Kami et al. |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,769,879 A | 6/1998 | Richards et al. |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Gon.cedilla.alves et al. |
| 5,919,219 A | 7/1999 | Knowlton |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,438,424 B1 | 8/2002 | Knowlton |
| 6,438,964 B1 | 8/2002 | Giblin |
| 6,453,202 B1 | 9/2002 | Knowlton |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,551,348 B1 * | 4/2003 | Blalock et al. .............. 607/104 |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,699,266 B2 | 3/2004 | Lachenbruch et al. |
| 6,718,785 B2 | 4/2004 | Bieberich |
| 6,746,474 B2 | 6/2004 | Saadat |
| 6,749,624 B2 | 6/2004 | Knowlton |
| 6,764,502 B2 | 7/2004 | Bieberich |
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |

| | | | | | | |
|---|---|---|---|---|---|---|
| 7,022,121 B2 | 4/2006 | Stern et al. | | EP | 0406244 A1 | 1/1991 |
| 7,037,326 B2 | 5/2006 | Lee et al. | | EP | 0598824 A1 | 6/1994 |
| 7,077,858 B2 | 7/2006 | Fletcher et al. | | GB | 2 286 660 A | 8/1995 |
| 7,081,111 B2 | 7/2006 | Svaasand et al. | | GB | 2323659 A | 9/1998 |
| 7,096,204 B1 | 8/2006 | Chen et al. | | JP | 63076895 A | 4/1988 |
| 7,112,712 B1 | 9/2006 | Ancell | | JP | 3259975 A | 11/1991 |
| 7,115,123 B2 | 10/2006 | Knowlton et al. | | JP | 4093597 A | 3/1992 |
| 7,183,360 B2 | 2/2007 | Daniel et al. | | JP | 7268274 A | 10/1995 |
| 7,189,252 B2 | 3/2007 | Krueger | | JP | 09164163 A | 6/1997 |
| 7,192,426 B2 | 3/2007 | Baust et al. | | JP | 10216169 A | 8/1998 |
| 7,204,832 B2 | 4/2007 | Altshuler et al. | | JP | 2005520608 T | 7/2005 |
| 7,220,778 B2 | 5/2007 | Anderson et al. | | JP | 2006026001 A | 2/2006 |
| 2002/0049483 A1 | 4/2002 | Knowlton | | KR | 1020040094508 | 11/2004 |
| 2002/0058975 A1 | 5/2002 | Bieberich | | SU | 532976 A1 | 11/1978 |
| 2002/0062142 A1* | 5/2002 | Knowlton ............ 607/99 | | TW | 0476644 | 2/2002 |
| 2002/0117293 A1 | 8/2002 | Campbell | | WO | WO-96/37158 | 11/1996 |
| 2002/0151887 A1 | 10/2002 | Stern et al. | | WO | WO-9636293 A1 | 11/1996 |
| 2002/0188286 A1 | 12/2002 | Quijano et al. | | WO | WO-97/05828 | 2/1997 |
| 2003/0069618 A1 | 4/2003 | Smith et al. | | WO | WO-9722262 A2 | 6/1997 |
| 2003/0079488 A1 | 5/2003 | Bieberich | | WO | WO-98/41157 | 9/1998 |
| 2003/0100936 A1 | 5/2003 | Altshuler et al. | | WO | WO-9938469 A1 | 8/1999 |
| 2003/0109908 A1 | 6/2003 | Lachenbruch et al. | | WO | WO 00/44346 | 8/2000 |
| 2003/0109910 A1 | 6/2003 | Lachenbruch et al. | | WO | WO-00/44349 | 8/2000 |
| 2003/0125649 A1 | 7/2003 | McIntosh et al. | | WO | WO-02/05736 A2 | 1/2002 |
| 2003/0199226 A1 | 10/2003 | Sommer et al. | | WO | WO-02/102921 | 12/2002 |
| 2003/0220674 A1 | 11/2003 | Anderson | | WO | WO-03/078596 A3 | 9/2003 |
| 2003/0236487 A1 | 12/2003 | Knowlton | | WO | WO-2004/000098 | 12/2003 |
| 2004/0006328 A1 | 1/2004 | Anderson | | WO | WO-2004080279 A2 | 9/2004 |
| 2004/0030332 A1 | 2/2004 | Knowlton et al. | | WO | WO-2005046540 A1 | 5/2005 |
| 2004/0039312 A1 | 2/2004 | Hillstead et al. | | WO | WO-2006066226 | 6/2006 |
| 2004/0049178 A1 | 3/2004 | Abboud et al. | | WO | WO-2006127467 | 11/2006 |
| 2004/0073079 A1 | 4/2004 | Altshuler et al. | | WO | WO-2007041642 A2 | 4/2007 |
| 2004/0074629 A1 | 4/2004 | Noel | | | | |
| 2004/0093042 A1 | 5/2004 | Altshuler et al. | | | | |
| 2004/0104012 A1 | 6/2004 | Zhou et al. | | | | |
| 2004/0162596 A1 | 8/2004 | Altshuler et al. | | | | |
| 2004/0199226 A1 | 10/2004 | Shadduck | | | | |
| 2004/0210214 A1 | 10/2004 | Knowlton | | | | |
| 2004/0210287 A1 | 10/2004 | Greene | | | | |
| 2004/0259855 A1 | 12/2004 | Anderson et al. | | | | |
| 2005/0049661 A1 | 3/2005 | Koffroth | | | | |
| 2005/0154431 A1 | 7/2005 | Quistgaard et al. | | | | |
| 2005/0159986 A1 | 7/2005 | Breeland et al. | | | | |
| 2005/0182462 A1 | 8/2005 | Chornenky et al. | | | | |
| 2005/0222565 A1 | 10/2005 | Manstein | | | | |
| 2005/0251120 A1 | 11/2005 | Anderson et al. | | | | |
| 2006/0030778 A1 | 2/2006 | Mendlein et al. | | | | |
| 2006/0036300 A1 | 2/2006 | Kreindel | | | | |
| 2006/0074313 A1 | 4/2006 | Slayton et al. | | | | |
| 2006/0079852 A1 | 4/2006 | Bubb et al. | | | | |
| 2006/0122509 A1 | 6/2006 | Desilets | | | | |
| 2006/0200063 A1 | 9/2006 | Munro et al. | | | | |
| 2006/0234899 A1 | 10/2006 | Nekmard et al. | | | | |
| 2006/0270745 A1 | 11/2006 | Hunt et al. | | | | |
| 2007/0010861 A1 | 1/2007 | Anderson et al. | | | | |
| 2007/0032561 A1 | 2/2007 | Lin et al. | | | | |
| 2007/0141265 A1 | 6/2007 | Thomson | | | | |
| 2007/0239075 A1 | 10/2007 | Rosenberg et al. | | | | |
| 2007/0249519 A1 | 10/2007 | Guha et al. | | | | |
| 2008/0077202 A1 | 3/2008 | Levinson | | | | |
| 2008/0140371 A1 | 6/2008 | Warner | | | | |
| 2008/0183164 A1 | 7/2008 | Elkins et al. | | | | |
| 2009/0118722 A1 | 5/2009 | Ebbers et al. | | | | |
| 2010/0081971 A1 | 4/2010 | Allison | | | | |

FOREIGN PATENT DOCUMENTS

| | | |
|---|---|---|
| DE | 532976 | 5/1974 |
| DE | 2851602 | 6/1980 |
| DE | 4213584 A1 | 11/1992 |
| DE | 4224595 | 1/1994 |
| EP | 0263069 A2 | 4/1988 |
| EP | 0397043 | 11/1990 |

OTHER PUBLICATIONS

Liu, A. Y.-C., et al., "Transient Cold Shock Induces the Heat Shock Response upon Recovery at 37° C. in Human Cells," J. Biol. Chem., May 20, 1994, 269(20), 14768-14775.

Nishikawa, "Ultrastructural Changes and Lipid Peroxidation in Rat Adipomusculocutaneous Flap Isotransplants after Normothermic Storage and Reperfusion," Transplantation,1992, 54, 795-801.

International Search Report for Applicant: PCT/US2007/075935; Zeltiq Aesthetics, Inc; Date of Mailing: Apr. 10, 2008 (4 pages).

Ardevol "Cooling rates of tissue samples during freezing with liquid nitrogen" J. of Biochem and Biophysical Methods, 27, 77-86 (1993).

Bondei, E. et al., "Disorders of Subcutaneous Tissue (Cold Panniculitis)," *Dermatology in General Medicine,* Chapter 108, Section 16: 1333-1334, 1993.

Burge, S.M. et al., "Hair Follicle Destruction and Regeneration in Guinea Pig Skin after Cutaneous Freeze Injury," *Cryobiology,* 27(2): 153-163, 1990.

Duncan, W.C. et al., "Cold Panniculitis," *Arch. Derm.,* 94: 722-24, 1966.

Epstein, E.H. et al., "Popsicle Panniculitis," *The New England Journal of Medicine,* 282(17):966-67, 1970.

Gage "Current Progress in Cryosurgery" Cryobiology 25, 483-486 (1988).

Hemmingsson "Attenuation in Human Muscle and Fat Tissue in Vivo and in Vitro" Acta Radiologica Diagnosis 23, 149-151 (1982).

Holman "Variation in cryolesion penetration due to probe size and tissue thermal conductivity" Ann. Thorac. Surg. 53, 123-126 (1992).

Hong, "Patterns of Ice Formation in Normal and Malignant Breast Tissue" Cryobiology 31, 109-120 (1994).

Kellum, R.E. et al., "Sclerema Neonatorum: Report of Case and Analysis of Subcutaneous and Epidermal-Dermal Lipids by Chromatographic Methods," *Arch. Derm.,* 97:372-80, 1968.

Koska, J. et al., "Endocrine Regulation of Subcutaneous Fat Metabolism During Cold Exposure in Humans," *Ann. N. Y. Acad, Sci.,* 967:500-05, 2002.

Laugier, et al., "In Vivo Results with a New Device for Ultrasonic Monitoring of Pig Skin Cryosurgery: The Echographic Cryprobe", The society for Investigative Dermatology, Inc., vol. 111 (2), Aug. 1998.

Maize, J.C., "Panniculitis," *Cutaneous Pathology*, Chapter 13: 327-344, 1998.

Malcom, G. et al., "Fatty Acid Composition of Adipose Tissue in Humans: Differences between Subcutaneous Sites," *Am. J. Clin. Nutr.*, 50(2): 288-91, 1989.

Moschella, S.L. et al., "Diseases of the Subcutaneous Tissue," *Derm.*, Section 2: 1169-1181, 1985.

Murphy, J.V. et al., "Frostbite: Pathogensesis and Treatment," *The Journal of Trauma: Injury, Infection, and Critical Care*, 48(1):171-178, 2000.

Pease "An Integrated Probe for Magnetic Resonance Imaging Monitored Skin Cryosurgery" Journal of Biomedical Engineering 117, 59-63, (1995).

Pech "Attenuation values, volume changes and artifacts in tissue due to freezing" Acta Radiologica 6, 779-782 (1987).

Phinney, S.D. et al., "Human Subcutaneous Adipose Tissue Shows Site-Specific Differences in Fatty Acid Composition," *Am. J. Clin. Nutr.*, 60: 725-29, 1994.

Rabi "Metabolic adaptations in brown adipose tissue of the hamster in extreme ambient temperatures" American Journal of Physiology 231, 153-160 (1976).

Renold, A.E., "Adipose Tissue," *Handbook of Physiology*, Chapter 15: 170-76, 1965.

Rubinsky "Cryosurgery: advances in the application of low temperatures to medicine" Int. J. Refrig. 190-199 (1991).

Young, H.E. et al., "Isolation of Embryonic Chick Myosatellite and Pluripotent Stem Cells," *J. Tiss. Cult. Meth.*, 14: 85-92, 1992.

U.S. Appl. No. 11/435,502, filed May 17, 2006, Levinson.

U.S. Appl. No. 11/528,189, filed Sep. 26, 2006, Levinson et al.

U.S. Appl. No. 11/528,225, filed Sep. 26, 2006, Levinson et al.

U.S. Appl. No. 11/741,271, filed Apr. 27, 2007, Levinson et al.

U.S. Appl. No. 11/750,953, filed May 18, 2007, Rosen et al.

U.S. Appl. No. 11/777,992, filed Jul. 13, 2007, Levinson et al.

U.S. Appl. No. 11/777,995, filed Jul. 13, 2007, Levinson et al.

U.S. Appl. No. 11/777,999, filed Jul. 13, 2007, Levinson et al.

U.S. Appl. No. 11/778,001, filed Jul. 13, 2007, Levinson et al.

U.S. Appl. No. 11/778,003, filed Jul. 13, 2007, Levinson et al.

Heller-Page et al., "Temperature-dependent skin disorders," Journal of the American Academy of Dermatology, May 1988, vol. 18, No. 5, Pt 1, pp. 1003-1019.

Henry et al., "Les Dermatoses Hivemales," Rev Med Liege, 1999, 54:11, 864-866. [Abstract Attached].

Nagore et al., "Lipoatrophia semicircularis-a traumatic panniculitis: Report of seven cases and review of the literature," Journal of the American Academy of Dermatology, Nov. 1998, 39:879-81.

Shephard, "Adaptation to Exercise in the Cold," Sports Medicine, 1985, 2:59-71.

Winkler et al., "Gene Transfer in Laboratory Fish: Model Organisms for the Analysis of Gene Function," Transgenic Animals, 1997, pp. 387-395.

U.S. Appl. No. 12/196,246, filed Aug. 21, 2008, Levinson.

U.S. Appl. No. 12/275,002, filed Nov. 20, 2008, Martens.

U.S. Appl. No. 12/275,014, filed Nov. 20, 2008, Martens.

U.S. Appl. No. 12/337,544, filed Dec. 17, 2008, Alison.

Bohm et al., "Saline-enhanced radiofrequency ablation of breat tissue: an in vitro feasibility study," Invest Radiol, 2000, pp. 149-157, vol. 35—issue (3).

Disclosure re: "Method and Apparatus for Regional Fat Reduction Using Controlled and Sustained Cooling of Skin Surface".

Donski et al., "The Effects of Cooling no Experimental Free Flap Survival," Brit J Plas Surg, 1980, pp. 353-360, vol. 33.

Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).

International Search Report and Written Opinion for PCT/US2007/023492; Applicant: Zeltiq Aesthetics, Inc.; Date of Mailing: May 15, 2008, 7 pages.

International Search Report and Written Opinion for PCT/US2007/064016; Applicant: Juniper Medical, Inc.; Date of Mailing: Jul. 20, 2007, 13 pages.

International Search Report and Written Opinion for PCT/US2007/064017; Applicant: Juniper Medical, Inc.; Date of Mailing: Oct. 26, 2007, 16 pages.

International Search Report and Written Opinion for PCT/US2007/064018; Applicant: Juniper Medical, Inc.; Date of Mailing: Jul. 26, 2007, 13 pages.

International Search Report and Written Opinion for PCT/US2007/067638; Applicant: Juniper Medical, Inc.; Date of Mailing: Jan. 10, 2008, 11 pages.

International Search Report and Written Opinion for PCT/US2007/069694; Applicant: Juniper Medical, Inc.; Date of Mailing: Nov. 23, 2007, 12 pages.

International Search Report and Written Opinion for PCT/US2007/083255; Applicant: Zeltiq Aesthetics, Inc.; Date of Mailing: Aug. 11, 2008, 8 pages.

International Search Report and Written Opinion for PCT/US2008/073930; Applicant: Zeltiq Aesthetics, Inc.; Date of Mailing: Nov. 7, 2008, 10 pages.

International Search Report and Written Opinion for PCT/US2007/062508; Applicant: Juniper Medical, Inc.; Date of Mailing: Jul. 20, 2007, 13 pages.

International Search Report for EP07758558.6; Applicant: Zeltiq Aesthetics, Inc.; Mailed on Jul. 20, 2007, 4 pages.

International Search Report for PCT/US2005/045988; (Apr. 25, 2006).

Kundu et al., "Breath acetone analyzer: diagnostic tool to monitor dietary fat loss," Clin Chem, 1993, pp. 87-92, vol. 39, issue (1).

Kundu et al., "Novel solid-phase assay of ketone bodies in urine," Clin Chem, 1991, pp. 1565-1569, vol. 37—issue (9).

Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).

Levchenko, et al., "Effect of dehydration on lipid metabolism," WMJ, 1978, pp. 95-97, vol. 50—issue (1).

Lidagoster, MD et al., "Comparison of Autologous Fat Transfer in Fresh, Refrigerated, and Frozen Specimens: An Animal Model Presented," at the 16th Annual Meeting of the Northeastern Society of Plastic Surgeons: Burlington, VT, 1999, pp. 512-515.

Lvova, "Lipid levels and lipid peroxidation in frog tissues during hypothermia and hibernation," WMJ, 1990, pp. 65-70, vol. 62—issue (1).

Nagao et al., "Dietary diacylglycerol suppresses accumulation of body fat compared to triacylglycerol in men a double-blind controlled trial," J Nutr, 2000, pp. 792-797, vol. 130—issue (4).

Nielsen, "Thermoregulation In Rest and Exercise," Acta Phys Scan Supp, 1969, pp. 6-74, vol. 323.

Non-Final Office Action; U.S. Appl. No. 11/435,502; Date of Mailing: Jul. 17, 2009, 10 pages.

Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.

Schoning, et al., "Experimental Frostbite: Freezing Times, Rewarming Times, and Lowest Temperatures of Pig Skin Exposed to Chilled Air," Cryobiology, 1990, pp. 189-193, 27.

Final Office Action; U.S. Appl. No. 10/391,221; Date of Mailing: Aug. 24, 2006, 4 pages.

Final Office Action; U.S. Appl. No. 11/016,196; Date of Mailing: Mar. 23, 2010, 12 pages.

Final Office Action; U.S. Appl. No. 11/435,502; Date of Mailing: Mar. 29, 2010, 11 pages.

International Search Report and Written Opinion for PCT/US2009/058088; Applicant: Zeltiq Aesthetics, Inc.; Date of Mailing: Nov. 20, 2009, 14 pages.

International Search Report and Written Opinion for PCT/US2009/067973; Applicant: Zeltiq Aesthetics, Inc.; Date of Mailing: Feb. 18, 2010, 10 pages.

Non-Final Office Action; U.S. Appl. No. 10/391,221; Date of Mailing: Jan. 25, 2006, 6 pages.

Non-Final Office Action; U.S. Appl. No. 10/391,221; Date of Mailing: May 30, 2007, 8 pages.
Non-Final Office Action; U.S. Appl. No. 10/391,221; Date of Mailing: Jul. 22, 2005, 6 pages.
Non-Final Office Action; U.S. Appl. No. 11/016,196; Date of Mailing: Apr. 22, 2008, 11 pages.
Non-Final Office Action; U.S. Appl. No. 11/016,196; Date of Mailing: Sep. 25, 2009, 8 pages.
Pre-Interview Office Action; U.S. Appl. No. 11/434,478; Date of Mailing: May 6, 2010, 4 pages.

* cited by examiner

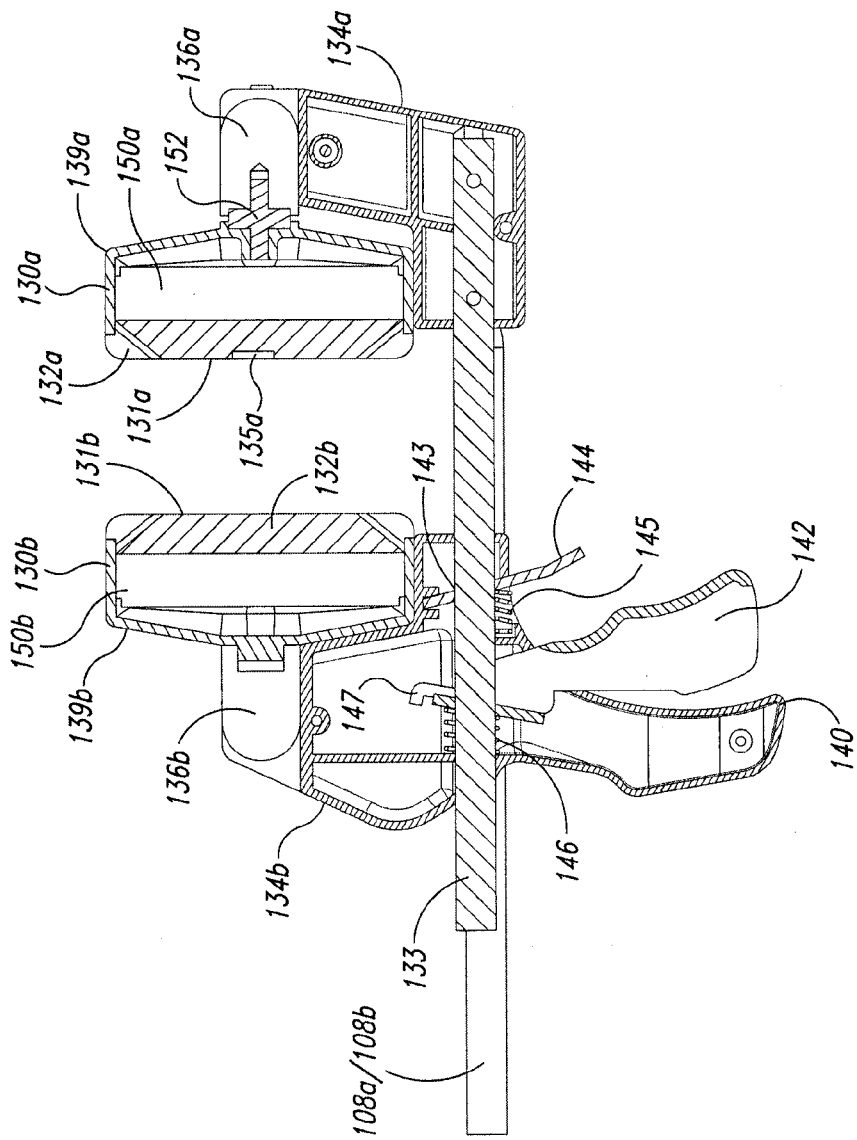
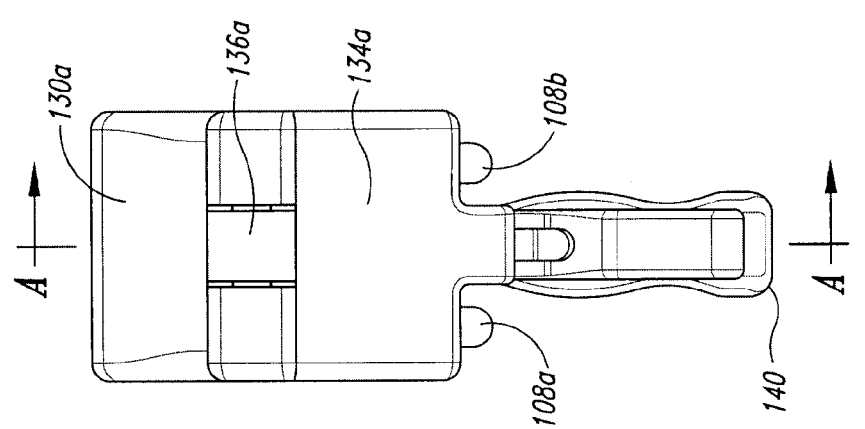
Fig. 3B
Fig. 3A

COOLING DEVICE FOR REMOVING HEAT FROM SUBCUTANEOUS LIPID-RICH CELLS

TECHNICAL FIELD

The present application relates to cooling devices, systems, and methods for removing heat from subcutaneous lipid-rich cells.

BACKGROUND

As statistics have shown, excess body fat increases the likelihood of developing various types of diseases such as heart disease, high blood pressure, osteoarthrosis, bronchitis, hypertension, diabetes, deep-vein thrombosis, pulmonary emboli, varicose veins, gallstones, hernias, and several other conditions.

In addition to being a serious health risk, excess body fat can also detract from personal appearance and athletic performance. For example, excess body fat can form cellulite that causes an "orange peel" effect at the surface of the skin. Cellulite forms when subcutaneous fat protrudes into the dermis and creates dimples where the skin is attached to underlying structural fibrous strands. Cellulite and excessive amounts of fat are often considered to be unappealing. Thus, in light of the serious health risks and aesthetic concerns associated with excess fat, an effective way of controlling excess accumulation of body fat is urgently needed.

Liposuction is a method for selectively removing body fat to sculpt a person's body. Liposuction is typically performed by plastic surgeons using specialized surgical equipment that mechanically removes subcutaneous fat cells via suction. One drawback of liposuction is that it is a serious surgical procedure, and the recovery may be painful. Liposuction can have serious and occasionally even fatal complications. In addition, the cost for liposuction is usually substantial.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using weight-loss drugs.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. The applied heat denatures fibrous septa made of collagen tissue and may destroy fat cells below the skin, and the cooling protects the epidermis from thermal damage. This method is less invasive than liposuction, but it still can cause thermal damage to adjacent tissue.

Another promising method of reducing subcutaneous fat cells is to cool the target cells as disclosed in U.S. Patent Publication No. 2003/0220674, the entire disclosure of which is incorporated herein. This publication discloses, among other things, reducing the temperature of lipid-rich subcutaneous fat cells to selectively affect the fat cells without damaging the cells in the epidermis. Although this publication provides promising methods and devices, several improvements for enhancing the implementation of these methods and devices would be desirable.

U.S. Patent Publication No. 2003/0220674 also discloses methods for selective removal of lipid-rich cells, and avoidance of damage to other structures including dermal and epidermal cells. A method for inducing collagen compaction, remodeling and formation is also needed for treatment of loose or sagging skin, age- or sun-damaged skin or a variety of other skin disorders. Therefore, a method for simultaneously removing lipid-rich cells while providing beneficial collagen effects is also needed.

BRIEF DESCRIPTION OF THE DRAWINGS

FIG. 3A is an end view and FIG. 3B is a side cross-sectional view partially illustrating a cooling device for removing heat from subcutaneous lipid-rich cells in accordance with an embodiment of the invention.

DETAILED DESCRIPTION

A. Overview

Figure 1:
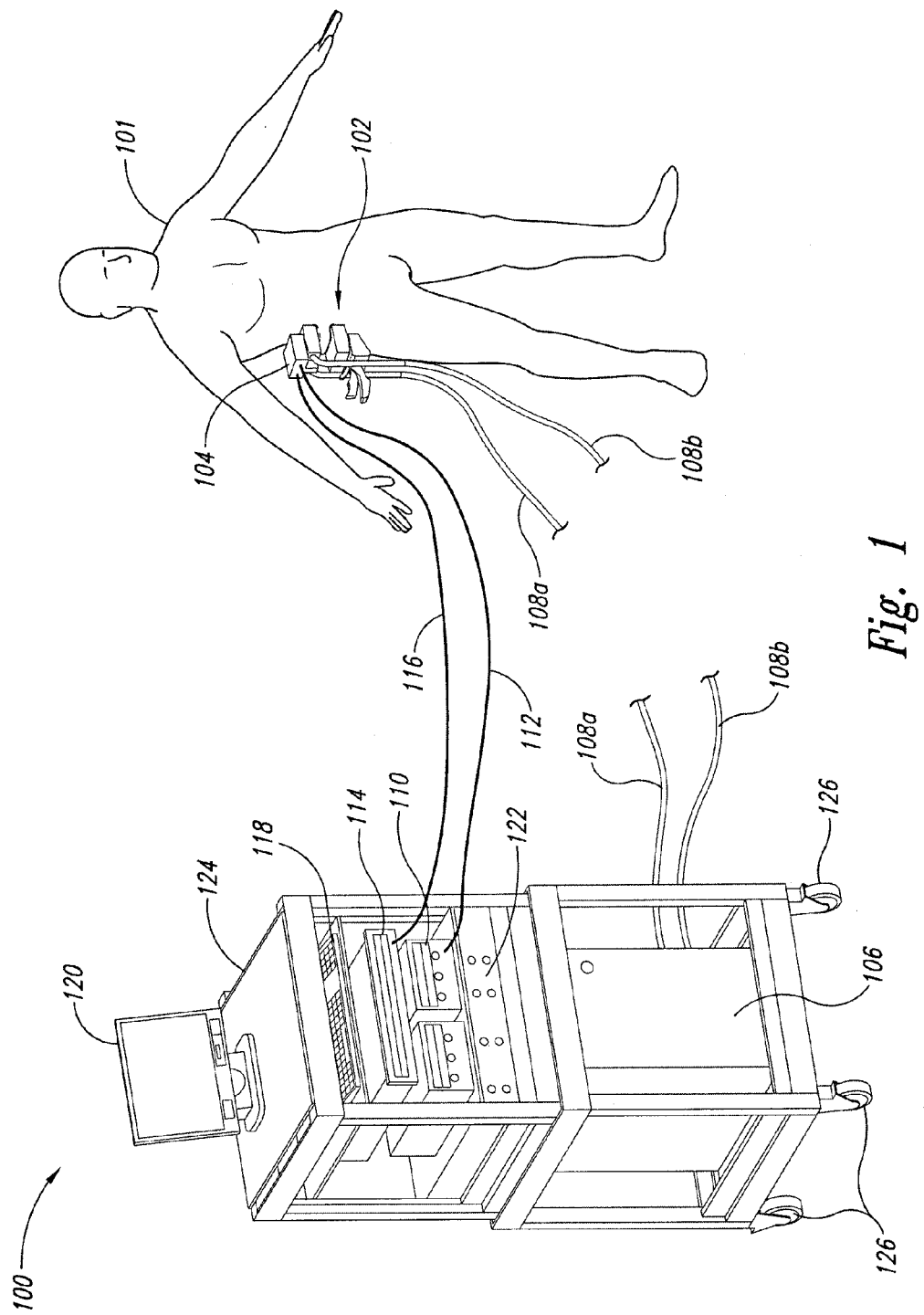
FIG. 1 is an isometric view of a system for removing heat from subcutaneous lipid-rich cells in accordance with an embodiment of the invention.

The present disclosure describes devices, systems, and methods for cooling subcutaneous lipid-rich cells. The term "subcutaneous tissue" means tissue lying underneath the dermis and includes adipocytes (fat cells) and subcutaneous fat. It will be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the invention. Additionally, the invention can include other embodiments that are within the scope of the claims but are not described in detail with respect to FIGS. 1-6.

One aspect is directed toward a cooling device for removing heat from subcutaneous lipid-rich cells. The cooling device includes a support with a first portion and a second portion, a first cooling element having a first heat exchanging surface, and a second cooling element having a second heat exchanging surface. The first cooling element is located at the first portion of the support, and the second cooling element is located at the second portion of the support. At least one of the first and second cooling elements is movable along the support, and at least one of the first and second cooling elements is configured to rotate for adjusting an angle between the first and second heat exchanging surfaces. The first and second cooling elements, for example, can be rotatable either in two dimensions or in three dimensions. The cooling elements can use a number of cooling technologies including thermoelectric coolers, recirculating chilled fluid, vapor compression elements, or phase change cryogenic devices. One skilled in the art will recognize that there are a number of other cooling technologies that could be used and that the cooling elements need not be limited to those described here. Further aspects include that the cooling device can be configured as a handheld device.

Another aspect is directed toward a cooling device having a cooling member using thermoelectric principles or other cooling technologies. The cooling device also includes a heat dissipating member in thermal communication with the cooling member and an interface member having a heat exchanging surface configured to contact a subject's skin. The cooling member can be capable of reducing a temperature of a region such that lipid-rich cells in the region are affected while non-lipid-rich cells are not generally affected. Further aspects include that the heat exchanging surface can be a curved surface for concentrating the cooling effects.

Another aspect is directed toward a method of applying a cooling device having two cooling elements rotatable relative to each other. The cooling elements can have heat exchanging surfaces capable of removing heat from the subject's skin. The method includes rotating the cooling elements to achieve a desired orientation between the two heat exchanging surfaces, cooling the heat exchanging surfaces of the two cooling elements to a desired temperature, placing the cooled heat exchanging surfaces proximate to the subject's skin, and reducing a temperature of a region such that lipid-rich cells in the region are affected while non-lipid-rich cells in the epidermis are not generally affected. Further aspects include holding the cooling device by at least one hand of an operator.

Another aspect is directed toward a system for removing heat from subcutaneous lipid-rich cells. The system includes a cooling device having two rotatable cooling elements capable of achieving a desired orientation between each other, and a heat sink coupled to the cooling device to dissipate heat generated by the cooling device. When placed proximate to a subject's skin, the two cooling elements can be capable of reducing a temperature of a region such that lipid-rich cells in the region are affected while non-lipid-rich cells in the epidermis and/or dermis are not generally affected. Further aspects include that the cooling device can be configured as a handheld device.

B. System for Selectively Reducing Lipid-rich Cells

FIG. 1 is an isometric view of a system 100 for removing heat from subcutaneous lipid-rich cells of a subject 101 in accordance with an embodiment of the invention. The system 100 can include a cooling device 104 placed at an abdominal area 102 of the subject 101 or another suitable area for removing heat from the subcutaneous lipid-rich cells of the subject 101. Various embodiments of the cooling device 104 are described in more detail below with reference to FIGS. 2-5.

The system 100 can further include a cooling unit 106 and fluid lines 108a-b connecting the cooling device 104 to the cooling unit 106. The cooling unit 106 can remove heat from a coolant to a heat sink and provide the chilled coolant to the cooling device 104 via the fluid lines 108a-b. Examples of the circulating coolant include water, glycol, synthetic heat transfer fluid, oil, a refrigerant and any other suitable heat conducting fluids. The fluid lines 108a-b can be hoses or other conduits constructed from polyethylene, polyvinyl chloride, polyurethane, and other materials that can accommodate the particular circulating coolant. The cooling unit 106 can be a refrigeration unit, a cooling tower, a thermoelectric chiller, or any other device capable of removing heat from a coolant.

As explained in more detail below, the cooling device 104 can include one or more thermoelectric cooling elements, such as Peltier-type thermoelectric elements. In such cases, the system 100 can further include a power supply 110 and a processing unit 114 operatively coupled to the cooling device 104. In one embodiment, the power supply 110 can provide a direct current voltage to the cooling device 104 to effectuate a heat removal rate from the subject 101. The processing unit 114 can monitor process parameters via sensors (not shown) placed proximate to the cooling device 104 and adjust the heat removal rate based on the process parameters. The processing unit 114 can include any processor, Programmable Logic Controller, Distributed Control System, and the like.

In another aspect, the processing unit 114 can be in electrical communication with an input device 118, an output device 120, and/or a control panel 122. The input device 118 can include a keyboard, a mouse, a touch screen, a push button, a switch, a potentiometer, and any other devices suitable for accepting user input. The output device 120 can include a display screen, a printer, a medium reader, an audio device, and any other devices suitable for providing user feedback. The control panel 122 can include indicator lights, numerical displays, and audio devices. In the embodiment shown in FIG. 1, the processing unit 114, power supply 110, control panel 122, cooling unit 106, input device 118, and output device 120 are carried by a rack 124 with wheels 126 for portability. In another embodiment, the various components can be fixedly installed at a treatment site.

One expected advantage of the system 100 is that the cooling device 104 can be applied to the subject 101 irrespective of the current physical condition of the subject 101. For example, the system 100 can be applied even when the subject 101 is not ambulatory or is ill. Another expected advantage is that the system 100 can remove or affect fat non-invasively without piercing the skin of the subject 101. Yet another expected advantage is that the system 100 is compact and can be used in an outpatient facility or a doctor's office. A further expected advantage is that the system 100 can quickly cool lipid-rich cells in a subcutaneous layer without requiring high-voltage power supplies.

C. Cooling Devices with Rotatable Cooling Elements

Figure 2A:
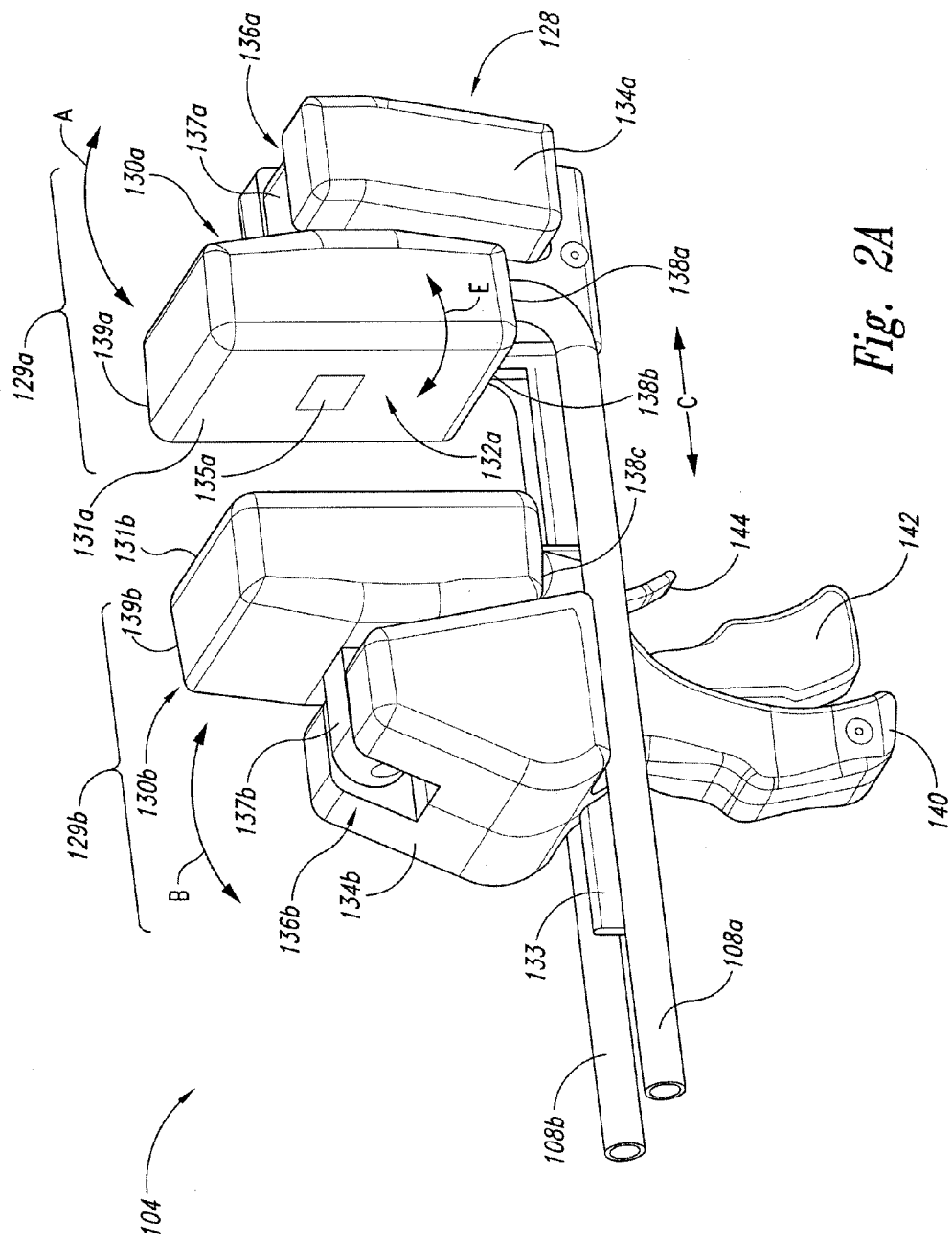
FIGS. 2A, 2B and 2C are isometric views of a cooling device for removing heat from subcutaneous lipid-rich cells in accordance with embodiments of the invention.

FIG. 2A is an isometric view of a cooling device 104 in accordance with one example of the invention suitable for use in the system 100. In this example, the cooling device 104 includes a support 128 having a first portion 129a and a second portion 129b, a first cooling element 130a located at the first portion 129a, and a second cooling element 130b located at the second portion 129b. The cooling device 104 is generally configured to be a handheld unit for manual operation, and/or it can be strapped or otherwise configured to be releasably attached to the subject. The first cooling element 130a and/or the second cooling element 130b can be configured to move along the support 128 and/or rotate to position the cooling elements 130a-b for applying pressure to the treatment area during operation. These features are described in more detail below with reference to specific examples of the cooling devices.

The first and second cooling elements 130a-b can have many similar features. As such, the features of the first cooling element 130a are described below with reference symbols followed by an "a", and corresponding features of the second cooling element 130b are shown and noted by the same reference symbol followed by a "b." The first cooling element 130a can include a housing 139a and fluid ports 138a-b coupled to the fluid lines 108a-b. The housing 139a can be constructed from polymeric materials, metals, ceramics, woods, and/or other suitable materials. The example of the housing 139a shown in FIG. 2A is generally rectangular but it can have any other desired shape.

The first cooling element 130a can further include a first interface member 132a having a first heat exchanging surface 131a for transferring heat to/from the subject 101. In one example, the first heat exchanging surface 131a is generally planar, but in other examples, the first heat exchanging surface 131a is non-planar (e.g., curved, faceted, etc.) The first interface member 132a can be constructed from any suitable material with a thermal conductivity greater than 0.05 Watts/Meter °Kelvin, and in many examples, the thermal conductivity is more than 0.1 Watts/Meter °Kelvin. Examples of suitable materials include aluminum, other metals, metal alloys, graphite, ceramics, some polymeric materials, composites, or fluids contained in a flexible membrane. As further described below with reference to FIGS. 4 and 5, portions of the first heat exchanging surface 131a can be an insulating material with a thermal conductivity less than 0.05 Watts/Meter °Kelvin.

The first cooling element 130a can also include at least one sensing element 135a proximate to the first heat exchanging surface 131a. The sensing element 135a, for example, can be generally flush with the heat exchanging surface 131a. Alternatively, it may be recessed or protrude from the surface. The sensing element 135a can include a temperature sensor, a pressure sensor, a transmissivity sensor, a bio-resistance sensor, an ultrasound sensor, an optical sensor, an infrared sensor, or any other desired sensor. In one example, the sensing element 135a can be a temperature sensor configured to measure the temperature of the first heat exchanging surface 131a and/or the temperature of the skin of the subject 101. For example, the temperature sensor can be configured as a probe or as a needle that penetrates the skin during measurement. Examples of suitable temperature sensors include thermocouples, resistance temperature devices, thermistors (e.g., neutron-transmutation-doped germanium thermistors), and infrared radiation temperature sensors. In another example, the sensing element 135a can be an ultrasound sensor configured to measure crystallization of subcutaneous fat in the treatment region of a subject. In yet another example, the sensing element 135a can be an optical or infrared sensor configured to monitor an image of the treatment region to detect, for example, epidermal physiological reactions to the treatment. The sensing element 135a can be in electrical communication with the processing unit 114 via, for example, a direct wired connection, a networked connection and/or a wireless connection.

The cooling device 104 can further include a mounting element 136a that couples the first cooling element 130a to the first portion 129a of the support 128. The mounting element 136a, for example, can be a pin, a ball joint, a bearing, or other types of rotatable joints. Suitable bearings include, but are not limited to, ball bearings, roller bearings, thrust bearings, and journal bearings. The mounting element 136a can accordingly be configured to rotatably couple the first cooling element 130a to the support 128. In certain embodiments, the first cooling element 130a can rotate relative to the support 128 in two dimensions (indicated by arrow A) such that the angle between the first and second heat exchanging surfaces 131a-b can be adjusted. In another embodiment, the first cooling element 130a can rotate in three dimensions relative to the support 128 (as indicated by arrows A and B).

Figure 2B:
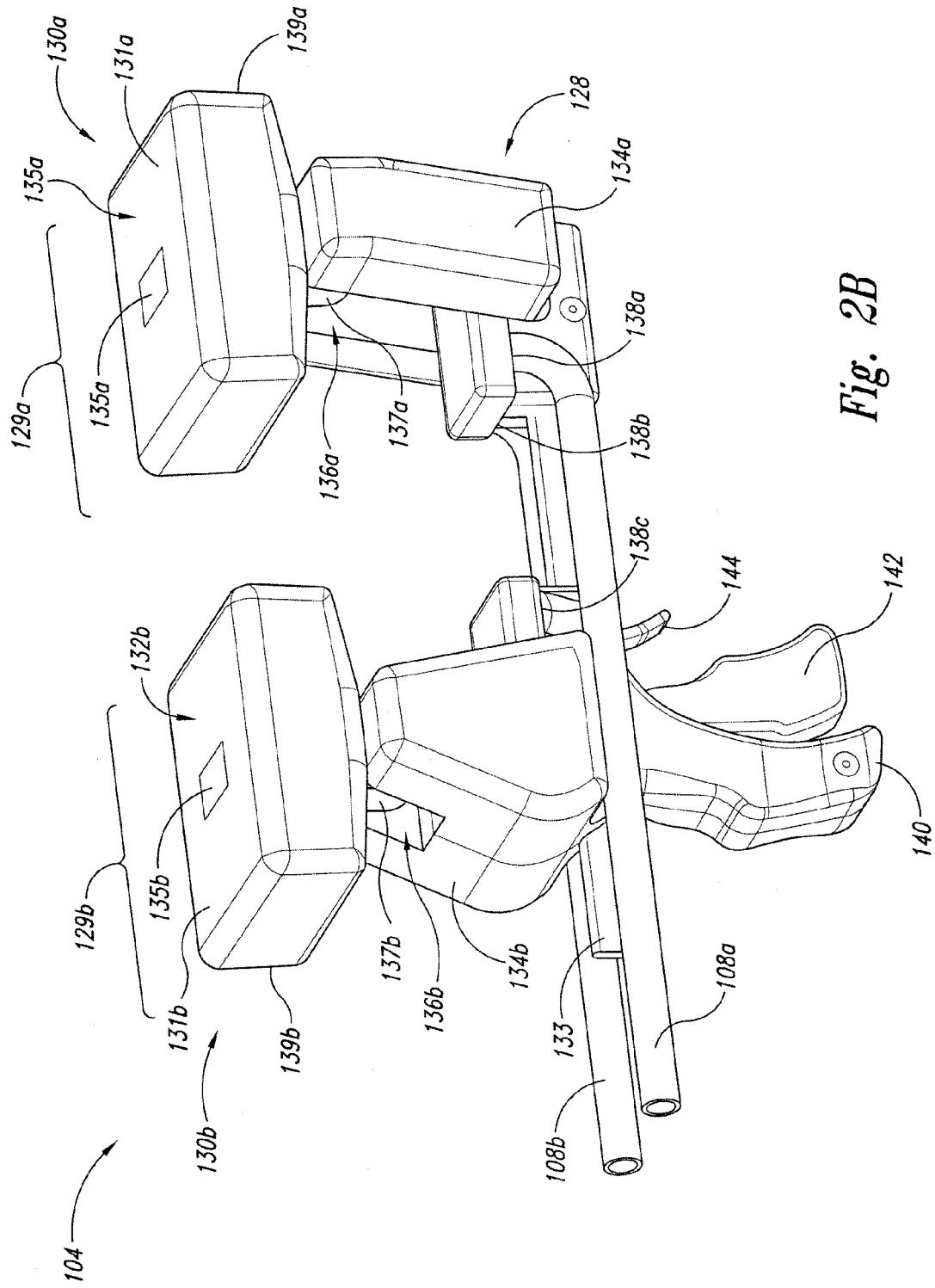

A specific example of the mounting element 136a includes a first mounting base 134a and a flange 137a coupled to the base 134a by a rotatable or pivotable joint. By rotatably mounting at least one of the first and second cooling elements 130a-b to the support 128, the angle between the first and second heat exchanging surfaces 131a-b can be adjusted. For example, as shown in FIG. 2A, the first and second cooling elements 130a-b can be generally parallel to each other, i.e., have an angle of generally 0° between the first and second heat exchanging surfaces 131a-b. As shown in FIG. 2B, the first and second cooling elements 130a-b can be generally co-planar, i.e., have an angle of generally 180° between the first and second heat exchanging surfaces 131a-b. With the rotatable mounting elements 136a-b, any angle of about 0° to about 180° between the first and second heat exchanging surfaces 131a-b can be achieved.

The cooling device 104 can further include a shaft 133, and the first mounting base 134a can be attached to the shaft 133. As explained in more detail below, at least one of the cooling elements 130a-b moves along the shaft 133 and/or the shaft 133 moves relative to the support 128 to adjust the distance between the first and second cooling elements 130a-b (shown by arrow C). The shaft 133, more specifically, extends between the first and second cooling elements 130a-b to enable movement of at least one of the cooling elements 130a-b relative to the support 128. In the embodiment shown in FIG. 2A, the first mounting base 134a is fixedly attached to the shaft 133, and a second mounting base 134b of the second cooling element 130b is configured such that the second mounting base 134b can slide along the shaft 133. In other embodiments, both the first mounting base 134a and the second mounting base 134b can be configured to slide along the shaft 133. The shaft 133 is generally constructed from polymeric materials, metals, ceramics, woods, or other suitable materials.

The cooling device 104 further includes a handle 140 slidably coupled to the shaft 133 or formed as a part of the shaft 133. The handle 140 is configured to be held by a hand of an operator. For example, the handle 140 can have a grip with grooves to improve stability of the cooling device 104 when held by the operator. The handle 140 further includes an actuator 142 that operates with the shaft 133 to move the second cooling element 130b relative to the shaft 133. In the example shown in FIG. 2A, the actuator 142 is a lever that engages the shaft 133 to incrementally advance the second cooling element 130b in an axial motion (arrow C) along the shaft 133.

In operation, an operator can hold the cooling device 104 in one hand by grasping the handle 140. Then, the cooling elements 130a-b can be rotated via the mounting elements 136a-b to achieve a desired orientation. The operator can place the cooling device 104 having the cooling elements 130a-b in the desired orientation proximate to the subject's skin to remove heat from a subcutaneous region of the subject 101. In one embodiment, the operator can clamp a portion of the subject's skin between the heat exchanging surfaces 131a-b when the surfaces 131a-b are generally parallel to each other. In another embodiment, the operator can press the heat exchanging surfaces 131a-b against the subject's skin when the surfaces 131a-b are generally co-planar. In certain embodiments, the operator can use thermoelectric coolers to remove heat from the subcutaneous region as described below with reference to FIG. 4. The operator can also monitor and control the treatment process by collecting measurements, such as skin temperatures, from the sensing element 135a. By cooling the subcutaneous tissues to a temperature lower than 37° C., subcutaneous lipid-rich cells can be selectively affected. The affected cells are then resorbed into the patient through natural processes.

One expected advantage of using the cooling device 104 is that subcutaneous lipid-rich cells can be reduced generally without collateral damage to non-lipid-rich cells in the same region. In general, lipid-rich cells can be affected at low temperatures that do not affect non-lipid-rich cells. As a result, lipid-rich cells, such as those forming the cellulite, can be affected while other cells in the same region are generally not damaged even though the non-lipid-rich cells at the surface are subject to even lower temperatures. Another expected advantage of the cooling device 104 is that it is relatively compact because the cooling device 104 can be configured as a handheld device. Yet another advantage is that the cooling device can be applied to various regions of the subject's body because the two cooling elements 130a-b can be adjusted to conform to any body contour. Another expected advantage is that by pressing the cooling device 104 against the subject's skin, blood flow through the treatment region can be reduced to achieve efficient cooling. Still another expected advantage is that the power requirement is reduced for each of the cooling elements 130a-b because heat is removed from the skin through the two heat exchanging surfaces 131a-b instead of a single cooling element.

The first and second cooling elements 130a-b can have many additional embodiments with different and/or additional features without detracting from the operation of both elements. For example, the second cooling element 130b may or may not have a sensing element proximate to the second heat exchanging surface 131b. The second cooling element 130b can be constructed from a material that is different from that of the first cooling element 130a. The second mounting base 134b can have a shape and/or a surface configuration different from that of the first mounting base 134a. The first cooling element 130a can be rotatable, but the second cooling element 130b may be non-rotatable.

Figure 2C:
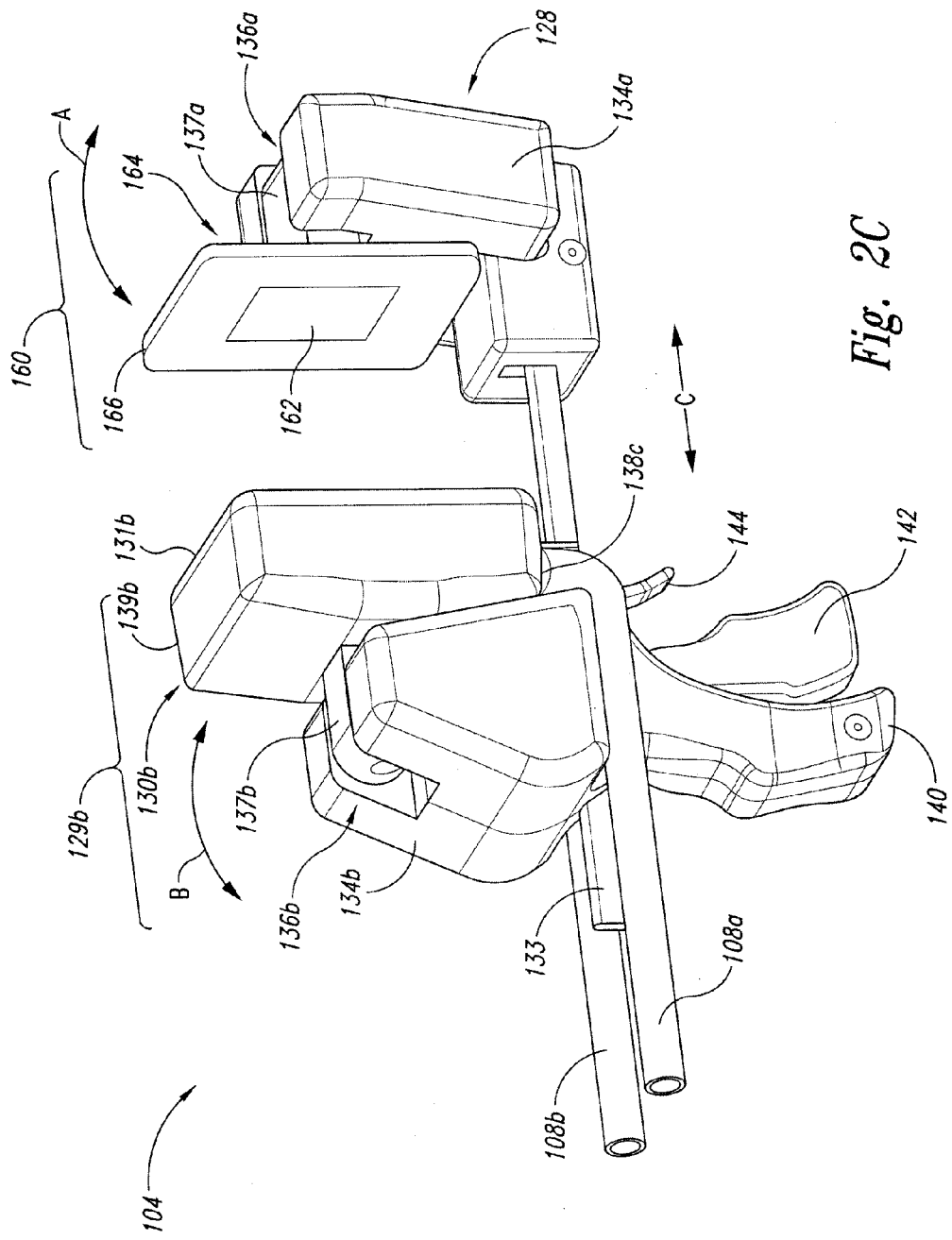

FIG. 2C is an alternative example of the cooling device 104 in accordance with one example of the invention for use in the system 100. This alternative example, and those alternative examples and other alternatives described herein, are substantially similar to previously-described examples, and common acts and structures are identified by the same reference numbers. Only significant differences in operation and structure are described below. In this example, the cooling device 104 includes a support 128 having a portion 129b and a portion 160, a cooling element 130b located at the portion 129b, and a reciprocating element 164 located at the portion 160. The cooling device 104 is generally configured to be a handheld unit for manual operation, and/or it can be strapped or otherwise configured to be releasably attached to the subject. In this example, the reciprocating element 164 can be configured to move along the support 128 and/or rotate to position the reciprocating element 164 to apply pressure to the treatment area during operation. The reciprocating element 164 can include a housing 166 and a sensing element 162. The housing 166 can be constructed from polymeric materials, metals, ceramics, woods, and/or other suitable materials. The example of the housing 166 shown in FIG. 2C is generally rectangular, but can have any other desired shape.

The reciprocating element 164 can also include at least one sensing element 162 proximate to the skin (not shown). The sensing element 162, for example, can be generally flush with a face of the reciprocating element 164. Alternatively, it may be recessed or protrude from the surface. The sensing element 162 can include a temperature sensor, a pressure sensor, a transmissity sensor, a bioresistance sensor, an ultrasound sensor, an optical sensor, an infrared sensor, or any other desired sensor, as discussed in detail herein.

FIG. 3A is an end view and FIG. 3B is a side elevation view of the embodiment of the cooling device 104 shown in FIGS. 2A and 2B. Like reference symbols refer to like features and components in FIGS. 1-3B. In one aspect, the first cooling element 130a can include a fluid chamber 150a within the housing 139a. The fluid chamber 150a can be in fluid communication with the fluid ports 138a-b such that fluid can circulate through the fluid chamber 150a. Optionally, the fluid chamber 150a can include one or more flow elements to promote uniform or otherwise controlled fluid circulation through the fluid chamber 150a. For example, the fluid chamber 150a can include baffles, static mixers, nozzles, ventures, orifices or any combination of these flow elements. The fluid chamber 150a can be configured to accept fluid coolants, such as water, glycol, a synthetic heat transfer fluid, oil, refrigerants, air, carbon dioxide, nitrogen, and argon.

The first interface member 132a can be a diffuser disposed in the housing 139a such that the first heat exchanging surface 131a faces away from the fluid chamber 150a. The first interface member 132a is accordingly in thermal communication with the fluid chamber 150a to transfer heat between the first heat exchanging surface 131a and the fluid chamber 150a. In one embodiment, the interface member 132a is releasably attached to the housing 139a using mechanical fasteners to allow access to the fluid chamber 150a or the backside of the first interface member 132a. The sensing element 135a can be placed in the first interface member 132a at least proximate to the first heat exchanging surface 131a as described above.

The first cooling element 130a can also include a pressure sensor 152 between the housing 139a and the mounting element 136a to sense the pressure exerted by the first cooling element 130a against the subject. In one embodiment, the first interface member 132a can be attached to the housing such that pressure applied against the first heat exchanging surface 131a is transferred via the housing 139a to the pressure sensor 152. The pressure sensor 152 can alternatively be configured to sense the pressure in the fluid chamber 150a for monitoring pressure variations in the fluid chamber 150a. Alternatively, the pressure could be inferred from force and the known contact area of the cooling elements. For example, the sensor 152 can be any type of load-sensitive pressure sensing element such as a load cell (model #LC201-25) produced by OMEGA Engineering, Inc. in Stamford, Conn. Direct pressure measurement could also be performed by placing a pressure measurement membrane directly at the interface between the cooling element and the skin.

The second cooling element 130b can also include a second interface member 132b similar to that of the first cooling element 130a. As shown in FIG. 3B, the second interface member 132b does not have a sensing element proximate to the second heat exchanging surface 131b. However, the second cooling element 130b can include a temperature sensor and/or a pressure sensor similar to the first cooling element 130a. In addition, the first and second cooling elements 130a-b can be configured to have different sensing elements.

FIG. 3B illustrates additional aspects of an example of the handle 140 and actuator 142. The actuator 142 can further include a spring 146 that drives the lever against a stop 147 fixedly attached to the second mounting base 134b. In operation, when an operator moves the actuator 142 toward the handle 140, the actuator 142 overcomes the force from the spring 146 to move the second mounting base 134b along the shaft 133 toward the first mounting base 134a. When the operator releases the actuator 142, the spring 146 drives the actuator 142 back in contact with the stop 147.

The cooling device 104 can further include a locking element that releasably holds the first and second cooling elements 130a-b in a fixed relative position. The locking element can be a catch 144 having a slot 143 through which the shaft 133 extends. A locking spring 145 forces the catch 144 to be at an angle relative to the shaft 133 such that the catch 144 frictionally engages the shaft 133. In operation, when an operator moves the actuator 142 toward the handle 140, the shaft 133 overcomes the force from the locking spring 145 to move the second mounting base 134b toward the first mounting base 134a. When the operator releases the actuator 142, the locking spring 145 drives the catch 144 away from the actuator 142 such that the catch 144 re-engages the shaft 133 to prevent the shaft 133 from slidably moving through the slot 143. When the operator moves the catch 144 toward the handle 140, the catch 144 disengages the shaft 133 to allow the shaft 133 to slide through the slot 143 so that the second cooling element 130b can be moved away from the first cooling element 130a. When the operator releases the catch 144, it re-engages the shaft 133 to prevent the shaft 133 from moving.

D. Method of Applying Cooling Devices with Rotatable Cooling Elements

In operation, the angle between the first and second heat exchanging surfaces 131a-b is selected by rotating the first and second cooling elements 130a-b. The angle between the cooling elements 130a-b is often selected to conform the first and second heat exchanging surfaces 131a-b to various body contours of the subject 101 and/or a desired clamping arrangement. In the embodiment shown in FIG. 2A, the angle between the first and second heat exchanging surfaces 131a-b can be generally 0°, i.e., the first and second heat exchanging surfaces 131a-b are generally parallel to each other for clamping a treatment region between the first and second cooling elements 130a-b. In the embodiment shown in FIG. 2B, the angle can be 180°, i.e., the first and second heat exchanging surfaces 131a-b are generally co-planar. In other embodiments, the angle can be any angle between generally 0° and generally 180°, as would be recognized by one skilled in the art.

After configuring the cooling elements 130a-b, an operator places the cooling device 104 proximate to the skin of the subject 101. In the embodiment shown in FIG. 2A (where the angle is generally 0°), the cooling elements 130a-b are initially spaced apart from each other by a first distance in which a fold of the patient's skin is placed. The operator then pulls the actuator 142 to drive the second cooling element 130b toward the first cooling element 130a until the fold of skin is clamped between the cooling elements 130a-b. The clamping force can be increased by using the actuator 142 or decreased by disengaging the catch 144. Optionally, the pressure sensor 152 can be used to sense the clamping pressure applied via the first interface member 132a, and the sensed clamping force can be processed by the processing unit 114 and displayed on the output device 120. The clamping force can then be adjusted based on the displayed values. The clamping force, for example, can be higher than the systolic pressure in the fold of skin to impede or block the blood flow into the fold of skin. As explained in more detail below, applying such pressure enables more effective cooling of the target region because there is less blood flow to transfer core body heat to the target region.

In another embodiment shown in FIG. 2B (where the angle is generally 180°), placing the cooling device 104 can include pressing the first and second heat exchanging surfaces 131a-b against an area of the subject's skin. In one aspect, the applied pressure on the subject's skin can be greater than or equal to the systolic blood pressure in the subject's skin. Optionally, the pressure sensor 152 can be used to sense the pressure applied via the first interface member 132a, and the pressure applied to the subject's skin can be adjusted as described above.

Clamping a fold of the subject's skin or pressing against the skin can be advantageous to achieve efficient cooling. In general, the subject 101 has a body temperature of about 37° C., and the blood circulation is one mechanism for maintaining a constant body temperature. As a result, blood flow through the dermis and subcutaneous layer of the region is a heat source that counteracts the cooling of the sub-dermal fat. As such, if the blood flow is not reduced, cooling the subcutaneous tissues would require not only removing the specific heat of the tissues but also that of the blood circulating through the tissues. Thus, reducing or eliminating blood flow through the target region can improve the efficiency of cooling and avoid excessive heat loss from the dermis and epidermis.

By cooling the subcutaneous tissues to a temperature lower than 37° C., subcutaneous lipid-rich cells can be selectively affected. In general, the epidermis and dermis of the subject 101 have lower amounts of unsaturated fatty acids compared to the underlying lipid-rich cells forming the subcutaneous tissues. Because non-lipid-rich cells usually can withstand colder temperatures better than lipid-rich cells, the subcutaneous lipid-rich cells can be selectively affected while maintaining the non-lipid-rich cells in the dermis and epidermis. An exemplary range for the cooling elements 130a-b can be from about −20° C. to about 20° C., preferably from about −20° C. to about 10° C., more preferably from about −15° C. to about 5° C., more preferably from about −10° C. to about 0° C.

The lipid-rich cells can be affected by disrupting, shrinking, disabling, destroying, removing, killing, or otherwise being altered. Without being bound by theory, selectively affecting lipid-rich cells is believed to result from localized crystallization of highly saturated fatty acids at temperatures that do not induce crystallization in non-lipid-rich cells. The crystals can rupture the bi-layer membrane of lipid-rich cells to selectively necrose these cells. Thus, damage of non-lipid-rich cells, such as dermal cells, can be avoided at temperatures that induce crystal formation in lipid-rich cells. Cooling is also believed to induce lipolysis (e.g., fat metabolism) of lipid-rich cells to further enhance the reduction in subcutaneous lipid-rich cells. Lipolysis may be enhanced by local cold exposure, inducing stimulation of the sympathetic nervous system.

In certain embodiments, once a desired temperature is achieved, the temperature of the region can be maintained for a pre-determined period of time. The cooling cycle can be terminated by separating the heat exchanging surfaces 131a-b from the skin. After a certain period of time, the cooling device 104 can be reapplied to the same portion of the skin as described above until a desired reduction in lipid-rich cells is achieved. In another embodiment, the cooling device 104 can be applied to a different portion of the skin as described above to selectively affect lipid-rich cells in a different subcutaneous target region.

One expected advantage of several of the embodiments described above is that the cooling device 104 can selectively reduce subcutaneous lipid-rich cells without unacceptably affecting the dermis, epidermis and/or other tissues. Another expected advantage is that the cooling device 104 can simultaneously selectively reduce subcutaneous lipid-rich cells while providing beneficial effects to the dermis and/or epidermis. These effects may include: fibroplasias, neocollagenesis, collagen contraction, collagen compaction, collagen density increase, collagen remodeling, and acanthosis (epidermal thickening). Another expected advantage is that the cooling device 104 can conform to various body contours of a subject by rotating the first and second cooling elements 130a-b to achieve a desired orientation. Yet, another expected advantage is that the cooling device 104 can be configured as a handheld device for ease of operation. Furthermore, another expected advantage is that the system 100 with the handheld cooling device 104 and the rack mounted processing unit 114 and cooling unit 106 are compact and efficient such that the method described above can be administered in an outpatient clinic or a doctor's office instead of in a hospital.

E. Cooling Devices with Thermoelectric Cooling Elements

Figure 4:
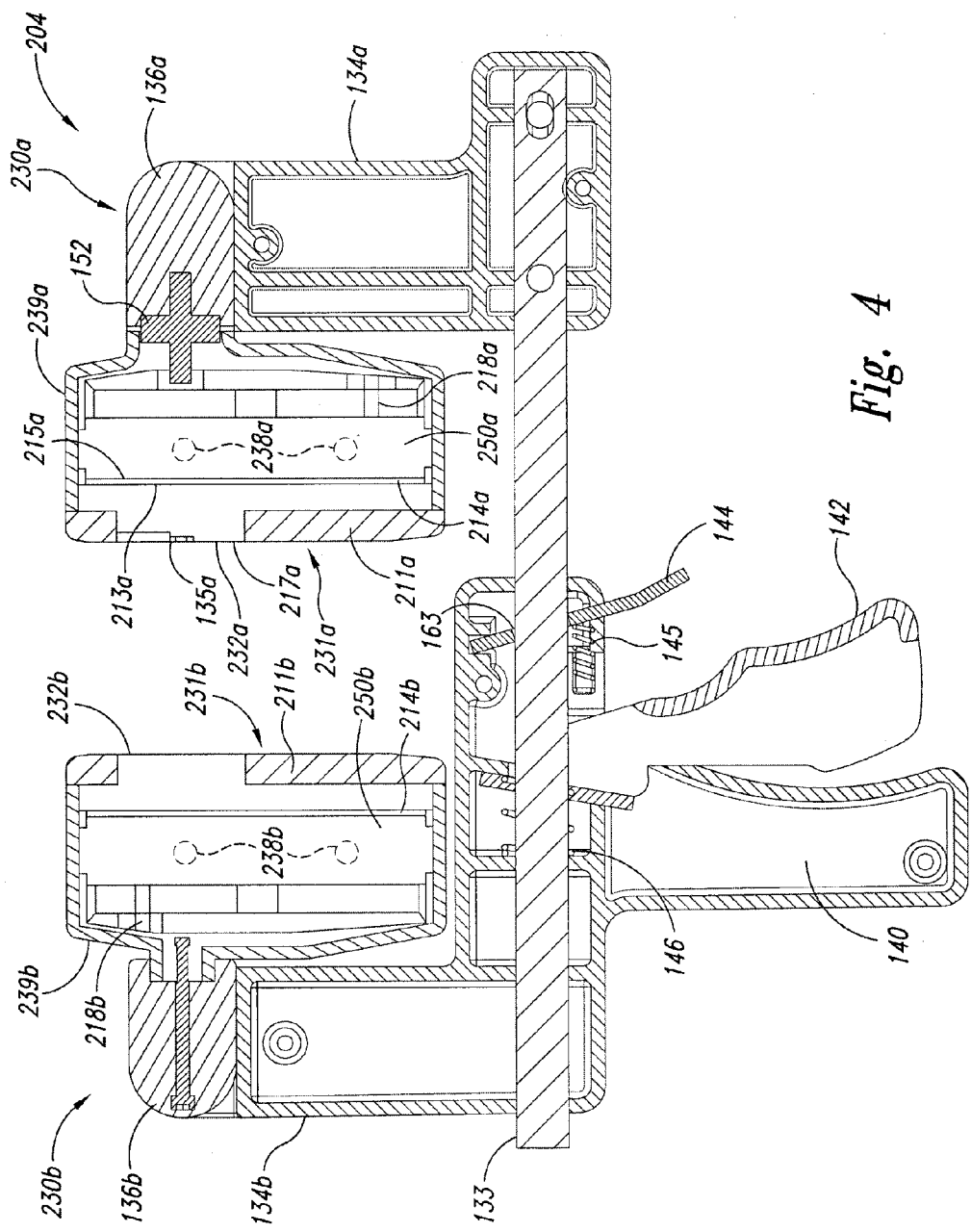
FIG. 4 is a side elevation view illustrating a cooling device having thermoelectric cooling elements in accordance with another embodiment of the invention.

FIG. 4 is a side elevation view of a cooling device 204 in accordance with another example of the invention. In this example, several components of the cooling device 204 are similar to the components of the cooling device 104 described above. As such, like reference symbols refer to like features and components in FIGS. 1-4. In this example, the cooling device 204 includes cooling elements 230a-b having thermoelectric cooling elements configured to reduce the temperature of a subcutaneous region of the subject 101 for selectively affecting lipid-rich cells in the region.

The first cooling element 230a can include a housing 239a and a plurality of fluid ports 238a coupled to the fluid lines 108a-b. The first cooling element 230a can also include a first interface member 232a having a first heat exchanging surface 231a and a first fluid chamber 250a. The first interface member 232a can be constructed with a thermally conductive material at the first heat exchanging surface 231a, but the first interface member 232a can have an insulating portion 211a around the first heat exchanging surface 231a.

The first cooling element 230a can further include a thermoelectric cooler 214a, such as a Peltier-type element, having a first side 213a and a second side 215a. The first side 213a is in thermal communication with the first interface member 232a, and the second side 215a is in thermal communication with the fluid chamber 250a. The thermoelectric cooler 214a can be connected to an external power supply (not shown) to transfer heat between the first side 213a and the second side 215a. The thermoelectric cooler 214a can be a single Peltier-type element or an array of Peltier-type elements. One suitable thermoelectric cooler is a Peltier-type cooling element (model # CP-2895) produced by TE Technologies, Inc. in Traverse City, Mich.

By applying power to the thermoelectric cooler 214a, heat can be effectively removed from the subject's skin via the first heat exchanging surface 231a to a circulating fluid in the fluid chamber 250a. For example, applying a current to the thermoelectric cooler 214a can achieve a temperature generally below 37° C. on the first side 213a of the thermoelectric cooler 214a to remove heat from the subject 101 via the first heat exchanging surface 231a. The thermoelectric cooler 214a transfers the heat from the first side 213a to the second side 215a where the heat is then transferred to the circulating fluid. The cooling unit 106 then removes the heat from the circulating fluid.

The thermoelectric coolers 214a-b can be configured to withdraw a sufficient amount of heat quickly from the subject 101 without using a high-voltage power supply for the cooling unit 106. In one example, the interface members 232a-b can be a generally rectangular aluminum plate with dimensions of about 3 cm×4 cm×1 cm, and the thermoelectric coolers are Peltier-type thermoelectric elements rated at about 160 Watts. As such, the cooling device 204 can cool a portion of the subject's skin (approximately 3 cm×4 cm×5 cm) from a temperature of about 37° C. to about −20° C. quickly and effectively. The cooling unit 106 can use a normal voltage power supply (e.g., 120 VAC) because the power consumption is not excessive. This enables the system to be used in hospitals, clinics, and small offices without more costly high voltage electrical systems.

The cooling device 204 can also be in electrical communication with the processing unit 114, and the cooling temperature can be automatically adjusted by the processing unit 114. The temperature of the first heat exchanging surface 231a can be sensed by the sensing element 135a. The sensed electrical signal can be converted by the processing unit 114 into a process value for the temperature. In one embodiment, the processing unit 114 can include a Proportional, Integral and Derivative controller, which can adjust the power output to the thermoelectric cooler 214a to achieve and/or maintain the desired temperature.

F. Cooling Devices with Curved Heat Exchanging Surfaces

Figure 5A:
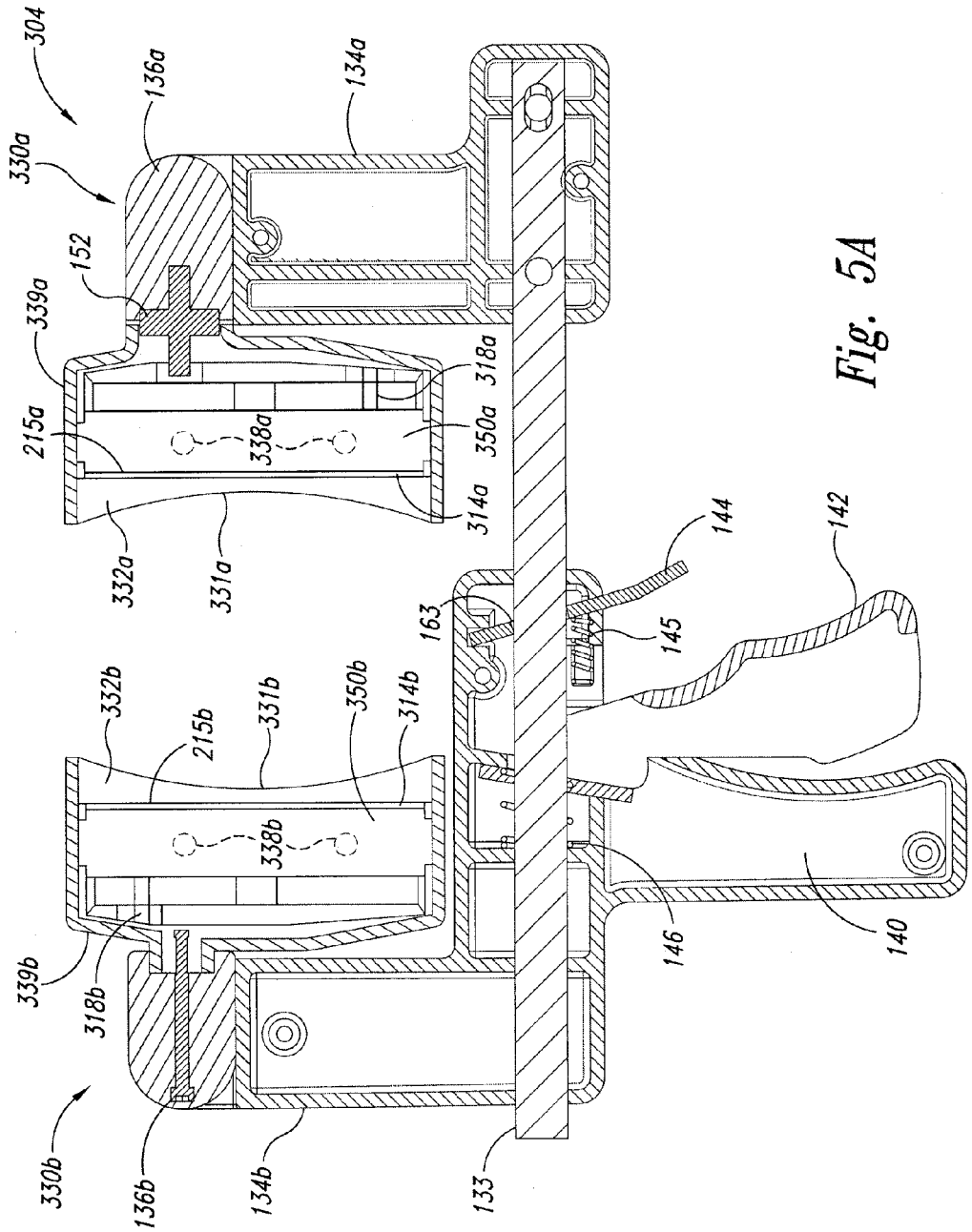
FIGS. 5A and 5B are side elevation views of a cooling device having curved heat exchanging surfaces in accordance with another embodiment of the invention.
Figure 5B:
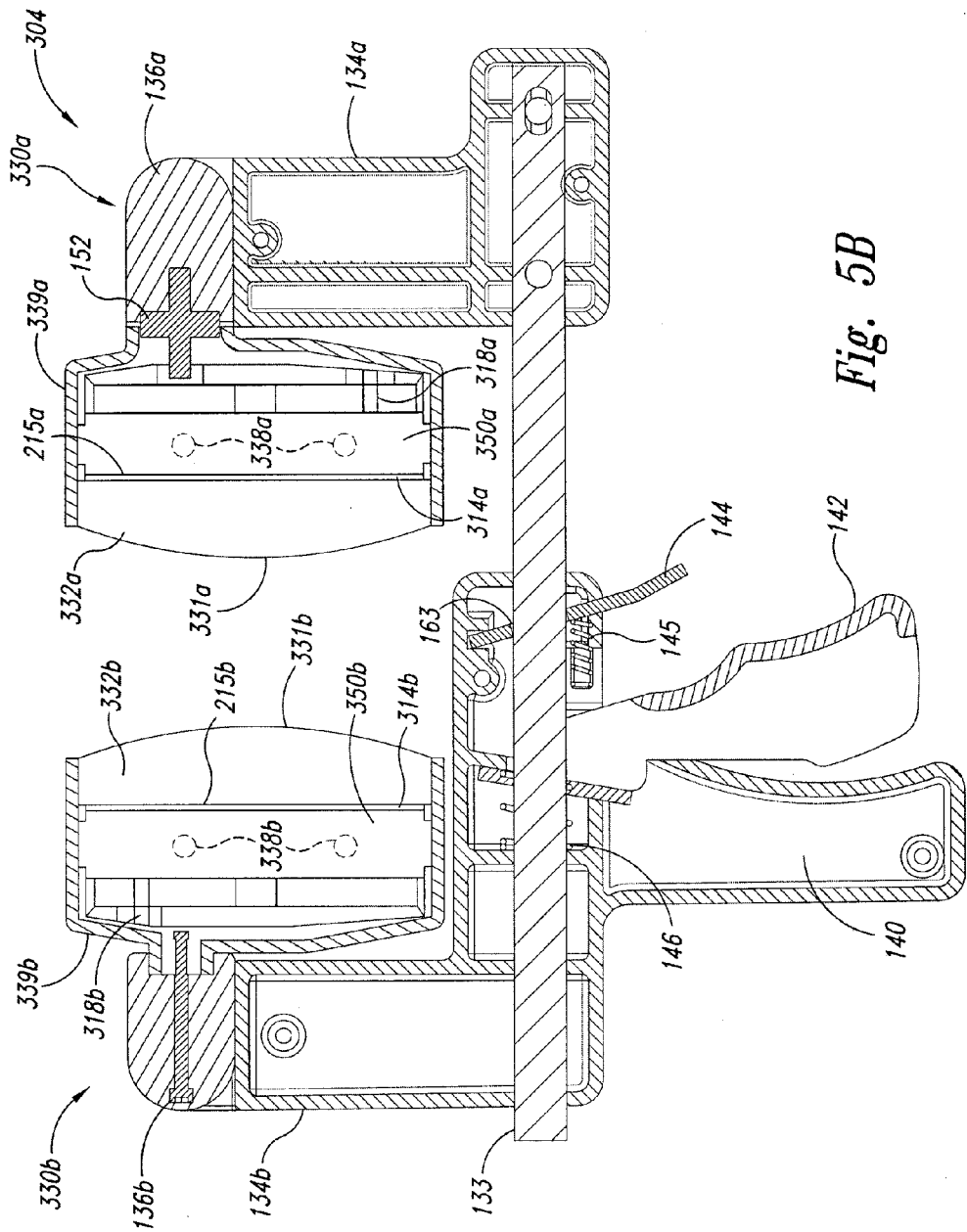

FIG. 5 is a side elevation view of a cooling device 304 in accordance with another example of the invention. Several components of the cooling device 304 are similar to those of the cooling device 104. As such, like reference symbols refer to like features and components in FIGS. 1-5. In this example, the cooling device 304 includes cooling elements 330a-b with curved heat exchanging surfaces 331a-b as described in more detail below.

The first cooling element 330a can include a housing 339a, a fluid chamber 350a, and fluid ports 338a coupled to the fluid lines 108a-b. The first cooling element 330a can further include an interface member 332a having a curved heat exchanging surface 331a and a back surface 333a. The curved heat exchanging surface 331a can be either concave or convex, and the back surface 333a can be either generally planar or similarly curved as the heat exchanging surface 331a. The first cooling element 330a can further include a thermoelectric cooler 314a proximate to the back surface 333a and in thermal communication with the fluid chamber 350a for removing heat via the heat exchanging surface 331a.

The second cooling element 330b in FIG. 5 includes similar features as the first cooling element 330a. Specifically, the second cooling element 330b includes a concave heat exchanging surface 331b with generally the same curvature as that of the heat exchanging surface 331a. However, the second cooling element 330b can also have a heat exchanging surface 331b that is concave but with a different curvature from that of the first heat exchanging surface 331a, or the heat exchanging surface 331b can be generally planar or convex. As such, the first and second heat exchanging surfaces 331a-b can have any combination of the different surface curvatures.

The first and second heat exchanging surfaces 331a-b operate generally similarly to the heat exchanging surfaces 131a-b of the cooling device 104. Particularly, the two curved first and second heat exchanging surfaces 331a-b can transfer heat to/from a portion of the skin when the portion of the skin is placed proximate to the first and second heat exchanging surfaces 331a-b. The curved surfaces 331a-b can enhance heat transfer from the portion of the skin as described below in more detail.

In operation, the cooling device 304 can be placed proximate to the skin of the subject 101 such that a portion of the skin is placed against the two curved heat exchanging surfaces 331a-b. Then the portion of the skin can be either clamped, strapped or pressed as described above with reference to FIGS. 2 and 3. In one embodiment, a voltage is applied to the thermoelectric coolers 314a-b to cool a subcutaneous region of the patient as described above with reference to FIG. 4. In further embodiments, other cooling methods can also be used, such as by convection, radiation, conduction, or any combination of these methods.

One advantage of the curved heat exchanging surfaces 331a-b is that the curved surfaces may focus the heat transfer in the subcutaneous region. For example, when both the heat exchanging surfaces are concave, the concave surfaces can focus heat removal from the skin between the two heat exchanging surfaces 331a-b. When both the heat exchanging surfaces are convex, the convex surfaces can spread the skin between the two heat exchanging surfaces 331a-b such that the distance between the subcutaneous layer of the skin and the heat exchanging surfaces 331a-b is reduced. The reduced distance may enhance heat transfer because the thermal conductivity of the epidermis and dermis decreases with decreased thickness.

G. Computing System Software Modules

Figure 6:
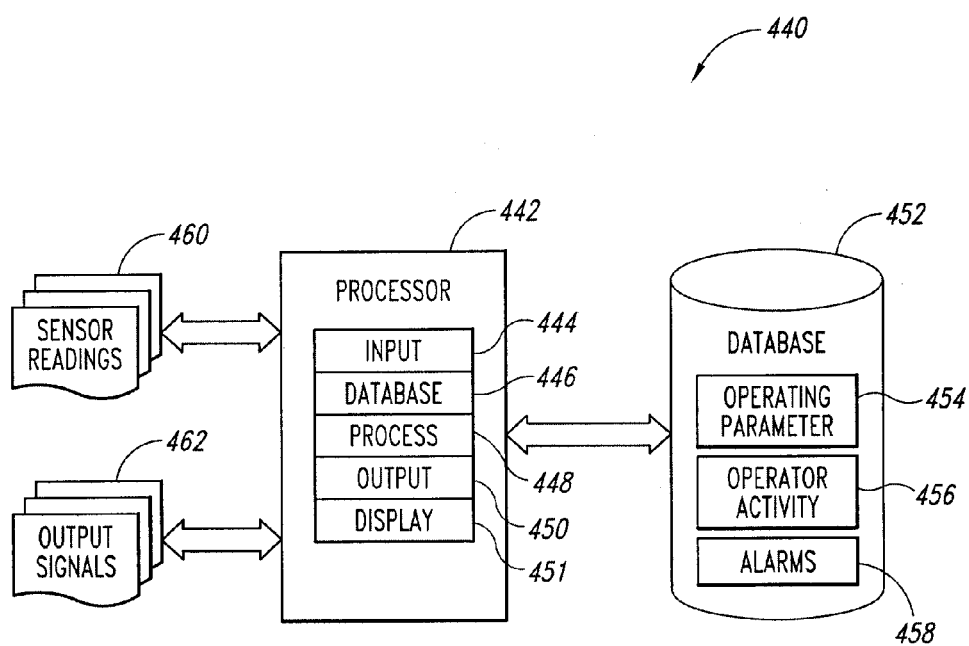
FIG. 6 is a block diagram showing computing system software modules for removing heat from subcutaneous lipid-rich cells.

FIG. 6 illustrates a functional diagram showing exemplary software modules 440 suitable for use in the processing unit 114. Each component can be a computer program, procedure, or process written as source code in a conventional programming language, such as the C++ programming language, and can be presented for execution by the CPU of processor 442. The various implementations of the source code and object and byte codes can be stored on a computer-readable storage medium or embodied on a transmission medium in a carrier wave. The modules of processor 442 can include an input module 444, a database module 446, a process module 448, an output module 450, and optionally, a display module 451. In another embodiment, the software modules 440 can be presented for execution by the CPU of a network server in a distributed computing scheme.

In operation, the input module 444 accepts an operator input, such as process setpoint and control selections, and communicates the accepted information or selections to other components for further processing. The database module 446 organizes records, including operating parameters 454, operator activities 456, and alarms 458, and facilitates storing and retrieving of these records to and from a database 452. Any type of database organization can be utilized, including a flat file system, hierarchical database, relational database, or distributed database, such as provided by a database vendor such as Oracle Corporation, Redwood Shores, Calif.

The process module 448 generates control variables based on the sensor readings 456, and the output module 450 generates output signals 458 based on the control variables. For example, the output module 450 can convert the generated control variables from the process module 448 into 4-20 mA output signals 458 suitable for a direct current voltage modulator. The processor 442 optionally can include the display module 451 for displaying, printing, or downloading the sensor readings 456 and output 458 via devices such as the output device 120. A suitable display module 451 can be a video driver that enables the processor 442 to display the sensor readings 456 on the output device 120.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A cooling device for removing heat from subcutaneous lipid-rich cells of a subject having skin, comprising:
   a support having a first portion and a second portion;
   a first cooling element having a first heat exchanging surface, and the first cooling element being located at the first portion of the support; and
   a second cooling element having a second heat exchanging surface, and the second cooling element being located at the second portion of the support, wherein at least one of the first and second cooling elements is movable along the support, and wherein at least one of the first and second cooling elements is configured to rotate for adjusting an angle between the first and second heat exchanging surfaces, wherein at least one of the first and second heat exchanging surface has a convex surface for reducing the distance between the heat exchanging surfaces for concentrating the cooling effects.

2. The cooling device of claim 1, wherein the angle between the first and second cooling elements can be adjusted from about 0° to about 180°.

3. The cooling device of claim 1, wherein the first and second cooling elements are rotatable in at least two dimensions.

4. The cooling device of claim 1, wherein the first heat exchanging surface has a reciprocal curvature to the curavature of the second heat exchanging surface.

5. The cooling device of claim 1, wherein at least a part of the first heat exchanging surface and at least a part of the second heat exchanging surface include a material having a thermal conductivity greater than about 0.1 Watts/Meter·° Kelvin.

6. The cooling device of claim 1, wherein a part of the first heat exchanging surface and a part of the second heat exchanging surface include a material having a thermal conductivity greater than about 0.05 Watts/Meter·° Kelvin.

7. The cooling device of claim 1, wherein the first and second heat exchanging surfaces each include a first part having a first material with a first thermal conductivity and a second part having a second material with a second thermal conductivity generally less than the first thermal conductivity.

8. The cooling device of claim 1, wherein at least one of the first and second cooling elements further comprises a fluid chamber in thermal communication with at least one of the first and second heat exchanging surfaces and a plurality of fluid ports in fluid communication with the fluid chamber, and wherein the fluid ports are configured to allow fluid circulation through the fluid chamber.

9. The cooling device of claim 8, wherein the fluid in communication with the fluid chamber is circulated through an external device which chills the fluid.

10. The cooling device of claim 1, wherein at least one of the first and second cooling elements further comprises a thermoelectric heat exchanger in direct thermal communication with at least one of the first and second heat exchanging surfaces.

11. The cooling device of claim 1, wherein at least one of the first and second cooling elements includes a housing, a fluid chamber in the housing, and a thermoelectric heat exchanger in the fluid chamber and in contact with a corresponding heat exchanging surface.

12. The cooling device of claim 11, wherein the housing further comprises a plurality of fluid ports configured to allow fluid circulation through the fluid chamber.

13. The cooling device of claim 1, wherein the first and second heat exchanging surfaces have reciprocal curvature.

14. The cooling device of claim 1, further comprising a temperature sensing element proximate to at least one of the first and second heat exchanging surfaces.

15. The cooling device of claim 1, further comprising a temperature sensing element and a pressure sensing element proximate to at least one of the first and second heat exchanging surfaces.

16. The cooling device of claim 1, further comprising:
a first temperature sensing element proximate to at least one of the first and second heat exchanging surfaces for detecting a temperature of a corresponding heat exchanging surface; and
a second temperature sensing element proximate to at least one of the first and second heat exchanging surfaces for detecting a temperature of the skin of the subject.

17. The cooling device of claim 1, further comprising a pressure sensing element proximate to at least one of the first and second heat exchanging surfaces.

18. The cooling device of claim 1, wherein the support comprises:
a first mounting base at the first portion;
a second mounting base at the second portion; and
a shaft coupled to the first and second mounting bases and guided for displacement.

19. The cooling device of claim 18, further comprising an actuator at the support and engaged with the shaft, and wherein the actuator is configured to displace the shaft.

20. The cooling device of claim 19, wherein the actuator further comprises a gripping element, the shaft being displaceable by moving the gripping element in a clamping direction to exert a clamping force between the first and second cooling elements.

21. The cooling device of claim 18, wherein the shaft is disposed in at least one of the first and second mounting bases.

22. The cooling device of claim 18, further comprising a locking element attached to the first or second mounting base for locking the first and second cooling elements in respective displaced positions.

23. The cooling device of claim 1, further comprising a handhold configured to be grasped by a hand of an operator.

* * * * *

UNITED STATES PATENT AND TRADEMARK OFFICE
CERTIFICATE OF CORRECTION

| | | |
|---|---|---|
| PATENT NO. | : 7,854,754 B2 | |
| APPLICATION NO. | : 11/359092 | |
| DATED | : December 21, 2010 | |
| INVENTOR(S) | : Joseph Ting et al. | |

It is certified that error appears in the above-identified patent and that said Letters Patent is hereby corrected as shown below:

On page 3, under "Other Publications", in column 2, line 36, delete "Cryprobe" and insert -- Cryoprobe --, therefor.

On page 4, under "Other Publications", in column 1, line 8, delete "Pathogensesis" and insert -- Pathogenesis --, therefor.

On page 4, under "Other Publications", in column 1, line 41, delete "Hivemales," and insert -- Hivernales, --, therefor.

On page 4, under "Other Publications", in column 1, line 55, delete "breat" and insert -- breast --, therefor.

On page 4, under "Other Publications", in column 1, line 63, delete "mahnesium," and insert -- magnesium, --, therefor.

On page 4, under "Other Publications", in column 2, line 37, delete "Refridgerated," and insert -- Refrigerated, --, therefor.

In column 7, line 59, delete "transmissity" and insert -- transmissivity --, therefor.

In column 14, lines 42-43, in Claim 4, delete "curavature" and insert -- curvature --, therefor.

Signed and Sealed this
Twenty-ninth Day of March, 2011

David J. Kappos
*Director of the United States Patent and Trademark Office*